(12) United States Patent
Hornscheidt et al.

(10) Patent No.: US 11,191,611 B2
(45) Date of Patent: Dec. 7, 2021

(54) MARKING DEVICE AND IMPLANTATION SYSTEM

(71) Applicant: Somatex Medical Technologies GmbH, Teltow (DE)

(72) Inventors: Dirk Hornscheidt, Berlin (DE); Tobias Jankowski, Berlin (DE)

(73) Assignee: SOMATEX MEDICAL TECHNOLOGIES GMBH, Teltow (DE)

( * ) Notice: Subject to any disclaimer, the term of this patent is extended or adjusted under 35 U.S.C. 154(b) by 413 days.

(21) Appl. No.: 16/302,921

(22) PCT Filed: Jun. 2, 2017

(86) PCT No.: PCT/EP2017/063509
§ 371 (c)(1),
(2) Date: Nov. 19, 2018

(87) PCT Pub. No.: WO2017/207777
PCT Pub. Date: Dec. 7, 2017

(65) Prior Publication Data
US 2019/0201160 A1    Jul. 4, 2019

Related U.S. Application Data

(60) Provisional application No. 62/379,891, filed on Aug. 26, 2016.

(30) Foreign Application Priority Data

Jun. 3, 2016 (DE) .......................... 102016110350.0
Feb. 24, 2017 (DE) .......................... 102017103957.0

(51) Int. Cl.
*A61B 90/00* (2016.01)
*A61B 10/02* (2006.01)
*A61B 17/00* (2006.01)

(52) U.S. Cl.
CPC .......... *A61B 90/39* (2016.02); *A61B 10/0283* (2013.01); *A61B 2017/00561* (2013.01);
(Continued)

(58) Field of Classification Search
CPC ........ A61B 17/12022; A61B 17/12172; A61B 2017/12054; A61B 2090/3966;
(Continued)

(56) References Cited

U.S. PATENT DOCUMENTS 4,863,470 A    9/1989    Carter
5,645,558 A    7/1997    Horton
(Continued)

FOREIGN PATENT DOCUMENTS

EP    0765636 A2    4/1997
EP    1 125 553 A1    8/2001
(Continued)

*Primary Examiner* — Mark D Remaly
(74) *Attorney, Agent, or Firm* — Jones Robb, PLLC

(57) ABSTRACT

Marking device (100) for implantation into a tissue (260), having a support structure (102) which is formed by at least one elastic metal wire, is compressible and is self-expanding and which, in an expanded state, encompasses an interior space (104), characterized in that the marking device (100) is designed to transform itself on its own from a compressed state into an expanded state, even against a tissue pressure prevailing at a tissue site to be marked, and the marking device (100) in the expanded state has a hollow, approximately spherical shape.

21 Claims, 9 Drawing Sheets

(52) U.S. Cl.
CPC .............. *A61B 2017/00862* (2013.01); *A61B 2017/00867* (2013.01); *A61B 2017/00898* (2013.01); *A61B 2017/00986* (2013.01); *A61B 2090/3925* (2016.02); *A61B 2090/3954* (2016.02); *A61B 2090/3966* (2016.02); *A61B 2090/3987* (2016.02); *A61B 2090/3991* (2016.02); *A61B 2090/3995* (2016.02)

(58) Field of Classification Search
CPC .............. A61B 90/39; A61B 17/12122; A61B 2017/00862; A61B 2017/00867; A61B 2017/00986; A61B 2017/1205; A61B 2090/3925; A61B 2090/3987; A61B 2090/3995; A61B 10/0283; A61B 17/0057; A61B 17/12031; A61B 17/12109; A61B 17/12113; A61B 17/12118; A61B 17/1215; A61B 17/12159; A61B 17/221; A61B 17/32056; A61B 2017/00477; A61B 2017/00526; A61B 2017/00539; A61B 2017/00561; A61B 2017/00575; A61B 2017/00579; A61B 2017/00592; A61B 2017/00597; A61B 2017/00619; A61B 2017/00623; A61B 2017/00632; A61B 2017/00898; A61B 2017/0412; A61B 2017/0427; A61B 2017/0464; A61B 2017/12068; A61B 2017/12095; A61B 2017/22035; A61B 2017/22038; A61B 2018/00416; A61B 2090/3908; A61B 2090/3954; A61B 2090/3982; A61B 2090/3991; A61F 2/01; A61F 2/011
See application file for complete search history.

(56) References Cited

U.S. PATENT DOCUMENTS

| | | |
|---|---|---|
| 5,766,219 A | 6/1998 | Horton |
| 6,090,125 A | 7/2000 | Horton |
| 6,254,633 B1 | 7/2001 | Pinchuk et al. |
| 6,356,782 B1 | 3/2002 | Sirimanne et al. |
| 6,371,904 B1 | 4/2002 | Sirimanne et al. |
| 6,428,558 B1 | 8/2002 | Jones et al. |
| 6,635,069 B1 | 10/2003 | Teoh et al. |
| 6,638,291 B1 | 10/2003 | Ferrera et al. |
| 6,725,083 B1 | 4/2004 | Burbank et al. |
| 6,766,186 B1 | 7/2004 | Hoyns et al. |
| 6,860,893 B2 | 3/2005 | Wallace et al. |
| 6,929,654 B2 | 8/2005 | Teoh et al. |
| 7,424,320 B2 | 9/2008 | Chesbrough et al. |
| 7,565,191 B2 | 7/2009 | Burbank et al. |
| 7,637,948 B2 | 12/2009 | Corbitt, Jr. |
| 7,668,582 B2 | 2/2010 | Sirimanne et al. |
| 8,060,183 B2 | 11/2011 | Leopold et al. |
| 8,112,869 B2 | 2/2012 | Jenks et al. |
| 8,224,424 B2 | 7/2012 | Burbank et al. |
| 8,280,486 B2 | 10/2012 | Miller et al. |
| 8,306,602 B2 | 11/2012 | Sirimanne et al. |
| 8,311,610 B2 | 11/2012 | Ranpura |
| 8,320,993 B2 | 11/2012 | Sirimanne et al. |
| 8,320,994 B2 | 11/2012 | Sirimanne et al. |
| 8,442,623 B2 | 5/2013 | Nicoson et al. |
| 8,480,706 B2 | 7/2013 | Chanduszko et al. |
| 8,600,481 B2 | 12/2013 | Sirimanne et al. |
| 8,718,745 B2 | 5/2014 | Burbank et al. |
| 8,747,597 B2 | 6/2014 | Rosqueta et al. |
| 9,095,342 B2 | 8/2015 | Becking et al. |
| 9,149,263 B2 | 10/2015 | Chanduszko |
| 9,216,069 B2 | 12/2015 | Foerster et al. |
| 9,271,736 B2 | 3/2016 | Heipl |
| 9,380,998 B2 | 7/2016 | Sirimanne et al. |
| D767,138 S | 9/2016 | Apostolidis |
| 9,492,570 B2 | 11/2016 | Sirimanne et al. |
| 9,526,648 B2 | 12/2016 | Sharma |
| 9,585,669 B2 | 3/2017 | Becking et al. |
| 9,669,113 B2 | 6/2017 | Sirimanne et al. |
| 9,861,346 B2 | 1/2018 | Callaghan |
| 9,986,974 B2 | 6/2018 | Sirimanne et al. |
| 10,156,030 B2 | 12/2018 | Koppe |
| 10,413,381 B2 | 9/2019 | Hermann et al. |
| 10,463,376 B2 | 11/2019 | Bodewadt et al. |
| 10,500,014 B2 | 12/2019 | Hermann et al. |
| 10,709,453 B2 | 7/2020 | Suzuki |
| 10,808,341 B2 | 10/2020 | Koppe |
| 2005/0049489 A1 | 3/2005 | Foerster et al. |
| 2006/0079805 A1 | 4/2006 | Miller et al. |
| 2007/0135826 A1 | 6/2007 | Zaver et al. |
| 2008/0097190 A1 | 4/2008 | Hornscheidt et al. |
| 2009/0000629 A1 | 1/2009 | Hornscheidt et al. |
| 2010/0063458 A1 | 3/2010 | Barr |
| 2010/0234726 A1 | 9/2010 | Sirimanne et al. |
| 2013/0018259 A1 | 1/2013 | Borillo et al. |
| 2013/0066195 A1 | 3/2013 | Sirimanne et al. |
| 2013/0123830 A1 | 5/2013 | Becking et al. |
| 2013/0211495 A1 | 8/2013 | Halden et al. |
| 2013/0289389 A1 | 10/2013 | Hermann et al. |
| 2014/0051996 A1 | 2/2014 | Sirimanne et al. |
| 2014/0243675 A1 | 8/2014 | Burbank et al. |
| 2014/0371778 A1 | 12/2014 | Rudakov et al. |
| 2015/0005804 A1 | 1/2015 | Franano et al. |
| 2015/0238197 A1 | 8/2015 | Quinn et al. |
| 2016/0074023 A1 | 3/2016 | Sakamoto et al. |
| 2016/0213380 A1 | 7/2016 | O'Brien et al. |
| 2016/0346453 A1 | 12/2016 | Mcguckin, Jr. et al. |
| 2017/0086852 A1 | 3/2017 | Martinez et al. |
| 2017/0086854 A1 | 3/2017 | Cragg et al. |
| 2017/0156733 A1 | 6/2017 | Becking et al. |
| 2017/0245864 A1 | 8/2017 | Franano et al. |
| 2017/0367710 A1 | 12/2017 | Yang |
| 2018/0206851 A1 | 7/2018 | Walzman |
| 2018/0344425 A1 | 12/2018 | Burbank et al. |
| 2019/0021810 A1 | 1/2019 | He et al. |
| 2019/0076212 A1 | 3/2019 | Liu |
| 2019/0175184 A1 | 6/2019 | Hui et al. |
| 2019/0201160 A1 | 7/2019 | Hornscheidt et al. |
| 2019/0262002 A1 | 8/2019 | Benjamin |
| 2019/0282325 A1 | 9/2019 | Alvarez et al. |
| 2019/0314034 A1 | 10/2019 | Cragg et al. |
| 2020/0054413 A1 | 2/2020 | Vogel |
| 2020/0113647 A1 | 4/2020 | Hermann et al. |
| 2020/0163659 A1 | 5/2020 | Cahill |
| 2020/0340154 A1 | 10/2020 | Koppe |
| 2020/0367904 A1 | 11/2020 | Becking et al. |
| 2021/0022765 A1 | 1/2021 | Walzman |

FOREIGN PATENT DOCUMENTS

| | | |
|---|---|---|
| EP | 1 782 745 A1 | 5/2007 |
| WO | 2006/000568 A2 | 1/2006 |
| WO | 2014153267 A1 | 3/2014 |
| WO | 2014168750 A1 | 10/2014 |
| WO | 2014169261 A1 | 10/2014 |
| WO | 2017051248 A1 | 3/2017 |
| WO | 2017162126 A1 | 9/2017 |
| WO | 2019118374 A1 | 6/2019 |
| WO | 2020243474 A1 | 12/2020 |

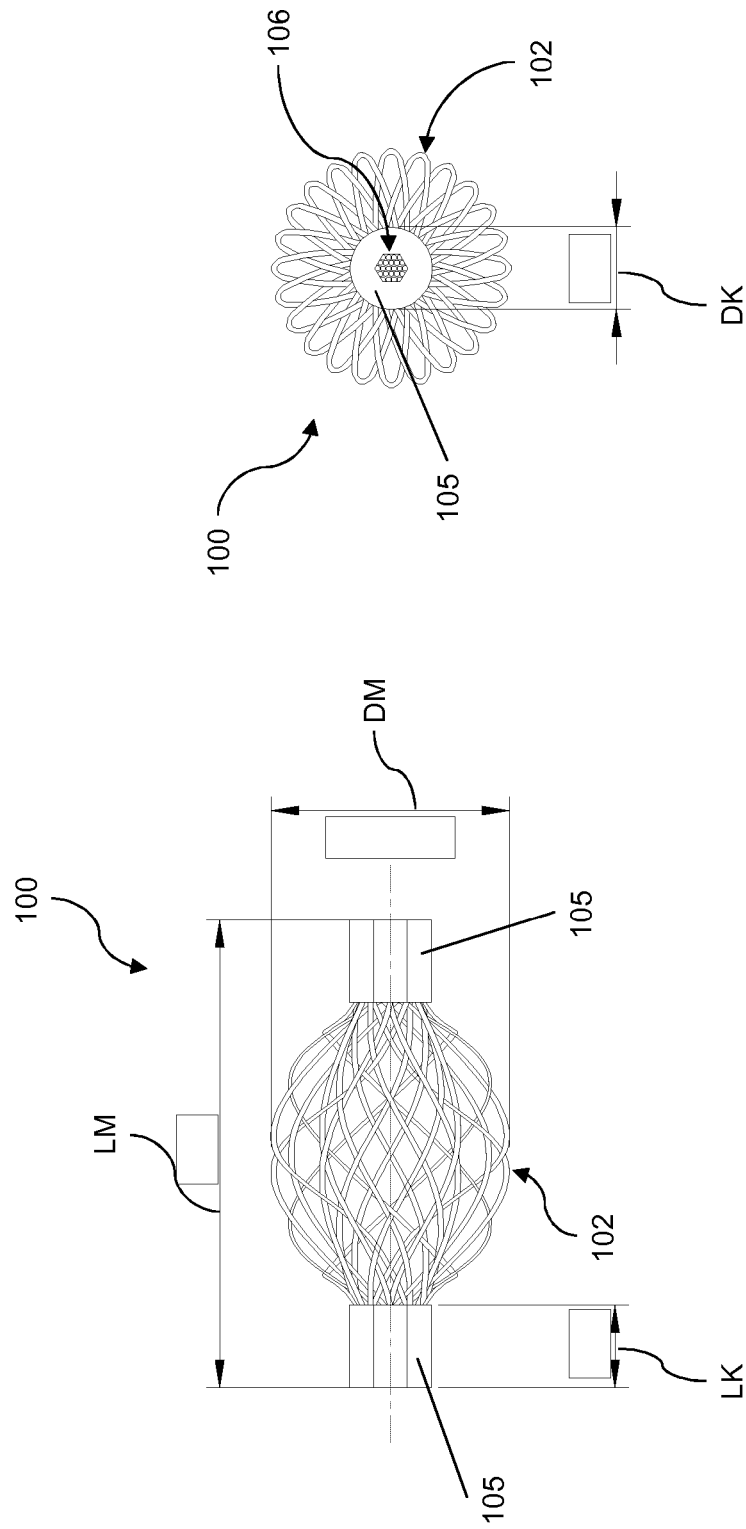

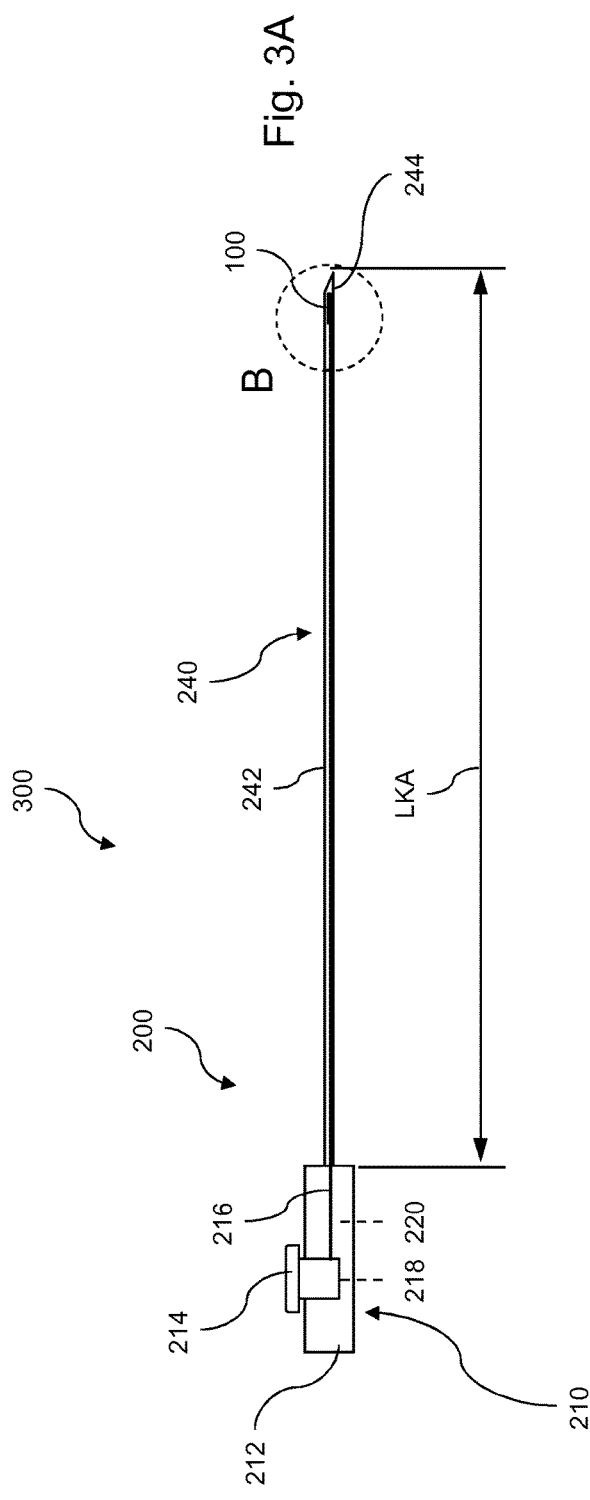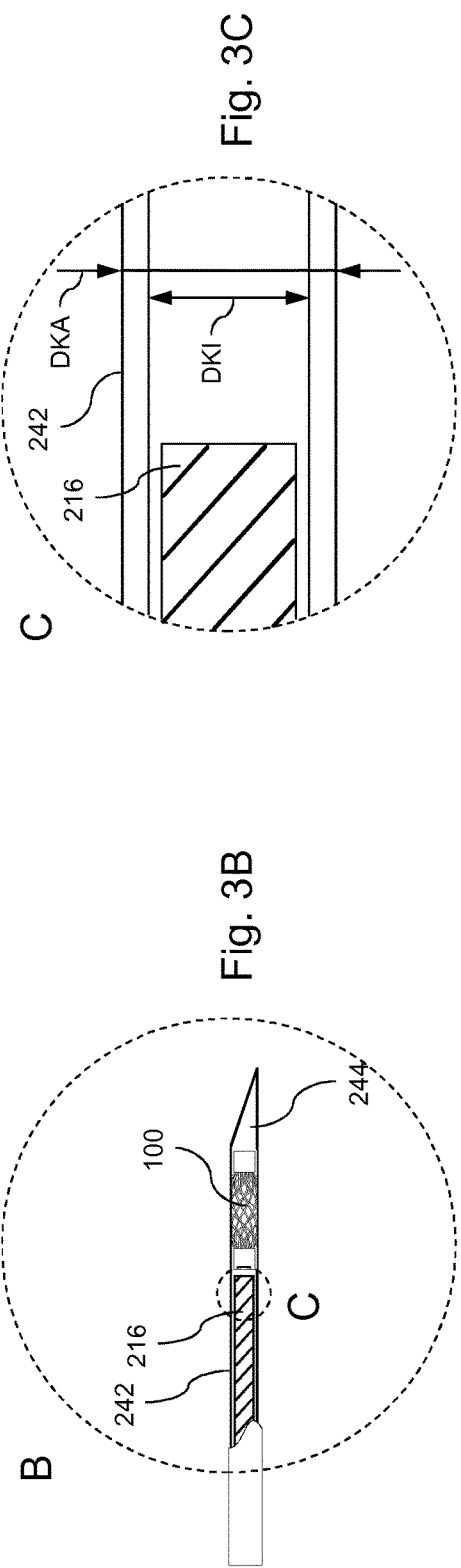

MARKING DEVICE AND IMPLANTATION SYSTEM

CROSS REFERENCE TO RELATED APPLICATIONS

This application is the U.S. National Stage of International Application Number PCT/EP2017/063509 filed on Jun. 2, 2017, which application claims priority under 35 USC § 120 to U.S. Provisional Patent Application 62/379,891 filed on Aug. 26, 2016 and claims priority under USC § 119 to German Patent Application No. 10 2016 110 350.0 filed on Aug. 26, 2016 and German Patent Application No. 10 2017 103957.0 filed on Feb. 24, 2017. All of these applications are hereby incorporated by reference in their entirety.

TECHNICAL FIELD

The invention relates to a marking device for implantation into a tissue, having an elastic, compressible and self-expanding support structure encompassing, in an expanded state, an interior space. The support structure can be formed by at least one metal wire. The invention further relates to an implantation system and to a method for implantation.

BACKGROUND OF THE INVENTION

Implantable marking devices for marking tissue sites are known in general. They are also referred to as tissue marker. Such marking devices are generally designed such that they can be implanted via a suitable implantation device into the tissue region to be marked in order to remain there permanently or over a certain period, for example between two surgical interventions. In this way, it is possible for treatment-relevant tissue, which comprises tumours or other tissue abnormalities for example, or potentially healthy tissue, which is to be monitored, to be marked for a relatively long period. The marking action of said marking devices is brought about by the visibility thereof during examination by means of imaging diagnostics methods, especially in the case of methods based on X-radiation, magnetic resonance or ultrasound waves.

WO 2006/000568 A2 discloses a marker for marking a tissue site after insertion of said marker using an applicator or a cannula of known construction. What this achieves is that the marker remains for a relatively long time in the tissue site to be marked and thus clearly marks a tissue site for later diagnostic and therapeutic steps. The marker consists of one or more wires which are twisted in the central marker segment and can have different shapes at the two end segments of the marker.

A surgical instrument, more particularly a marker instrument for marking body tissue segments, is further described in EP 1 782 745 B1. It is intended that the instrument be suited in particular to marking tumour tissue before the surgical removal of said tissue.

A manufacturing method for producing spherical cage structures consisting of nitinol from the area of operative orthopaedics for the treatment of bone necrosis is disclosed in U.S. Pat. No. 8,112,869 B2. The cage structures produced according to the method described therein are intended for stabilizing the femoral head, by being inserted in compressed form via a channel drilled through the femur, by expanding in the femoral head and by cavities then being filled with compacted bone graft. In this area of application, the diameters of the cage structures vary between 20 and 30 mm.

U.S. Pat. No. 9,216,069 B2 describes a breast biopsy marker system in which a multiplicity of marker elements are preloaded in compressed form in a delivery tube, said marker elements containing at least one radiopaque wire segment.

U.S. Pat. No. 8,060,183 B2 discloses in general a cavity-encompassing marker for the purposes of marking for breast biopsies in imaging methods. In one variant, the marker consists of an outer hollow body closed at both longitudinal ends and a smaller permanent marker situated within the outer body. Furthermore, it is stated that the outer hollow body consists of a bioabsorbable material and degrades over a certain period, whereas the inner permanent marker continues to remain in the tissue.

SUMMARY OF THE INVENTION

It is an object of the invention to specify an improved marking device for implantation into a tissue.

The object, relating to the marking device, is achieved according to the invention by means of a marking device of claim 1. The marking device for implantation into a tissue has a support structure which is formed by at least one elastic metal wire or a slit tube, is compressible and is self-expanding. The marking device, in an expanded state, encompasses an interior space. The elastic, compressible and self-expanding support structure can, however, also be made from plastic or contain plastic, for example PEEK. The marking device is designed to transform itself on its own from a compressed state into an expanded state, even against a tissue pressure prevailing at a tissue site to be marked, and to assume in the expanded state a hollow, approximately spherical shape.

Such a marking device can advantageously meet two requirements: it firstly offers a good visibility under ultrasound and secondly counteracts a migration of the marker in tissue just after implantation.

If a biopsy, for example a vacuum biopsy, should have been carried out prior to marking, the tissue pressure acting against the direction of spread of the marking device may, owing to a cavity that is already present, accordingly be lower or not present. In such a case, the expansion of the marking device after placement prevents the marking device from falling back into the biopsy cannula or prevents rinse-out through the pierce channel of the vacuum biopsy unit.

As a further aspect of the invention, an implantation system comprising a marking device and an implantation device is proposed. As a likewise further aspect of the invention, a method is proposed, comprising the steps of compressing the marking device in an implantation device, advancing the cannula into the tissue, deploying the marking device at the tissue site to be marked, expanding the marking device, and removing the cannula from the tissue. Lastly, a further implantation system is proposed, which can be guided within an inner volume of a vacuum biopsy cannula up to the location of the biopsy previously carried out and can release there the marking device for implantation through an instrument-specific lateral deployment opening.

The invention is based on the consideration that the visibility of marking devices is to be ensured even for imaging methods based on different principles of action. Furthermore, it is intended that the unambiguous and distinct visibility of marking devices under a largest possible spectrum of examination conditions and applications be ensured. In the case of ultrasound-based imaging methods, a good identifiability of the marker is yielded by a highest possible sound reflection of the support structure formed by metal or hard plastic, and a high transmission of the space which is enclosed by the expanded support structure and which can be hollow or filled with interstitial fluid or hydrogel. The combination of high sound reflection by the expanded support structure and low sound reflection by the interior space enclosed thereby brings about a good identifiability under ultrasound.

In the case, too, of X-radiation-based imaging methods such as, for example, mammography, a high absorption of X-radiation by the support structure especially in combination with a low absorption of X-radiation by the interior space enclosed by the support structure leads to a good identifiability in the X-ray image. The high absorption of X-radiation by the support structure is caused by the metal of the support structure, for example the metal wires or plastic-embedded metal particles. The high transmission of the interior space arises from the high transmission of air, water or hydrogel for X-radiation.

In the case of magnetic resonance imaging (MRI), the magnetic properties of the material of the marking device lead to the good identifiability thereof.

The method according to the invention avoids in particular the circumstance which generally occurs in the methods presented at the start, wherein the relative alignment of the marking device in relation to the direction of action or penetration of the imaging method influences the visibility thereof. This disadvantageous circumstance is especially caused by marking devices according to the approaches presented at the start that are implanted by means of a cannula and therefore generally have a longitudinal, thin shape. If such a longitudinal marking device is aligned such that a largest possible cross section is penetrated, a relatively high, unambiguous visibility of the marking device in the imaging method is ensured. However, if such a longitudinal marking device is aligned such that only a small cross section is penetrated, the visibility of the marking device in the imaging method is low or, in the worst case, not present.

By contrast, the marking device according to the invention is based on the insight that achieving a best possible marking action requires the marking device to have a shape which does not fall short of a minimum cross section in all directions of penetration, in particular which cross section is especially substantially larger than the cross section of the cannula used for implantation.

The marking device according to the invention achieves the advantages of long-term marking of tissue sites by means of implantable marking devices, while ensuring an unambiguous, alignment-independent visibility in imaging methods.

The invention is also based on the insight that, in addition, it is not only the size of the cross section, but also the shape of the cross section, which has a substantial influence on the visibility of the marking device. The more uniform the appearance of the marking device in the particular imaging method under different conditions and relative alignments, the more easily can the marking device be recorded by a person, in particular by a physician.

A marking device shape meeting these requirements is the sphere, since it forms, in all planes of projection, a cross-sectional area which is both uniformly round and equally large. Also, the image of the marking device, which image is round or is spherical in three-dimensional imaging methods, forms an artefact which unambiguously stands out from the majority of the other tissue structures and which can be easily identified. Exceptions here are, at most, enclosed tissue encapsulations, such as cysts for example, which have a similar shape in imaging methods. However, a distinguishing criterion generally consists in the intensity of a marking device at its outer surface, which, owing to its material properties, is depicted in imaging methods as a hyperechoic border surrounding the spherical interior space.

The concept preferably provides the basis for a marking device which is visible in an improved manner and which can be placed and implanted in tissue via a cannula. The advantage of the marking device lies in its alignment-independent visibility in imaging methods, especially in the case of ultrasound-based methods. The cavity enclosed by the spherical marking device after expansion fills with body fluid owing to the permeability of the support structure. Body fluid (or else hydrogel) offers a high sound transmission and therefore barely reflects ultrasound, whereas the expanded support structure strongly reflects sound. Thus, the implanted (and hence also expanded and thus approximately spherical) marking device is visible as a circle in the ultrasound image, independently of the direction of penetration of the ultrasound waves, and is therefore unambiguously identifiable.

Advantageous developments of the invention are to be found in the dependent claims and specify in detail advantageous ways of realizing the above-explained concept in the context of the stated object and with respect to further advantages.

In particular, it is envisaged that the support structure is woven, braided, wound or knitted. The advantage here consists in the economically viable manufacturability of a structure which spreads across an area and which, in a subsequent production step, is brought into a hollow, approximately spherical shape.

Alternatively, the support structure can be formed by a wire or tube which is slit in the longitudinal direction and which is axially compressed with respect to its original longitudinal direction, meaning that the segments separated from one another by the slits arch outward and that the structure is shortened. If the shortened, arched outward state of such a support structure is the relaxed state thereof, the support structure is self-expanding.

A further alternative for the support structure is a support structure composed of plastic, for example a basket made in an injection-moulding process, composed of PEEK for example.

Furthermore, it is advantageously envisaged that the support structure is formed from at least not more than five wires, preferably exactly one wire. A low number of wires leads in particular to the advantage that the entire marking device has only a few wire ends, just two in the case of one wire, which wire ends are to be directed into the interior space of the marking device.

In a likewise advantageous variant, the support structure is formed by a multiplicity of wires which are held together at their longitudinal ends by sleeves or caps.

In the context of a further preferred development, it is envisaged that all wire ends of the support structure are located in the interior space of the marking device. This leads to the advantage that no wire ends protrude from the spherical surface of the marking device, and thus the risk of injuring tissue bordering the marking device is significantly lowered.

In particular, it is envisaged that the wire diameter is less than 0.5 mm, preferably less than or equal to 0.1 mm. In this case, a low wire diameter has a positive effect on the compressibility of the marking device, which compressibility is required in implantation via a cannula having a lowest possible diameter. By contrast, a larger wire diameter has a positive effect on the expansion force of the support structure of the marking device. This leads to the marking device being able to expand even against a tissue pressure prevailing in hard tissue, for example tumour tissue.

Furthermore, it is advantageously envisaged that the diameter of the marking device in the expanded state is less than 8 mm, preferably 2.0-4.0 mm. A marking device in this diameter range represents a compromise between, on the one hand, visibility in imaging methods and, on the other hand, the space requirement of a foreign body in tissue.

A marking device in the expanded state having a certain minimum size offers the advantage that it can be palpated by a surgeon during treatment.

Furthermore, it is advantageously envisaged that the diameter of the marking device in its laterally compressed state is less than 3 mm, preferably less than 1.0 mm. A low diameter in the compressed state or a high compressibility of the marking device allows an implantation of the marking device using a relatively thin cannula, i.e. a cannula having a low diameter. Using a low diameter lowers the risk of injury and pain for the patient, and it is more frequently possible, in the context of simplified handling, to dispense with a stab incision and/or anaesthetization. The result of this is, additionally, advantages with respect to duration and costs of use.

In the context of a further preferred development, it is envisaged that the wire consists of or comprises nitinol. Owing to the material properties of nitinol as superelastic material, this leads to the advantage that the marking device, after deployment from the implantation device, transforms itself on its own from a compressed state into an laterally expanded state, especially against the pressure of the tissue bordering the marking device, which pressure is acting against the direction of expansion. Also, the use of further superelastic materials and/or shape-memory alloys is possible.

A rapid self-expansion of the marking device after its implantation, which self-expansion is ensured by the use of nitinol for example, is crucial for preventing a migration of the marking device, especially just after implantation.

Furthermore, it is advantageously envisaged that the material of the support structure is not absorbable. This aspect of the invention leads to the advantage that the marking device generally residing in tissue over a relatively long period does not degrade. By applying such non-absorbable material, it is also prevented that the marking device disadvantageously interacts with the adjacent tissue, especially through the release of ingredients or material constituents of the support structure to the adjacent tissue.

In particular, it is envisaged that the marking device has at least one fastening means for fixing the support structure. Said at least one fastening means can in particular be formed by a clamp, sleeve or the like, which can be crimped, welded or adhesively bonded and thus fixes the support structure. In one specific manifestation, a multiplicity of wires forming the support structure can, at their two respective ends, be brought together in parallel in a fitted nitinol sleeve and be firmly connected, for example welded, thereto.

This variant gives rise to the advantage that the marking device can be formed in a simplified production method especially from a tubular wire structure, for example by the closure of both ends of a tubular segment in order to shape an approximately spherical support structure. In the case, too, of embodiments with a support structure consisting of only a few wires or a single wire, the use of fastening means may be advantageous, for example for fixing individual wires or wire segments relative to one another. For example, it is possible to generate a device body by means of a single wire by appropriate back and forth motion during placement and subsequent fixation of the wire segments at the turning points.

The wires of a support structure formed by a multiplicity of wires need not all consist of the same material. On the contrary, individual wires composed of other materials can also be interlaced as well in order to optimize visibility in magnetic resonance imaging or else to increase X-ray visibility in computed tomography or under C-arms. Suitable materials are, for example, titanium, gold, iron-containing alloys and/or nitinol.

Instead of a nitinol sleeve, it is also possible to use other clamps, for example caps or sleeves composed of a different material. Such clamps can also have different shapes. Thus, the clamps can differ from one another in terms of shape and length for example. This makes it possible to use marking devices having different clamps, meaning that individual marking devices can be individually identified even after implantation.

If the two clamps, sleeves or caps of a marking device differ in terms of their shape, in particular length, it is possible to identify better the alignment of the marker in tissue.

Further differentiating features of individual marking devices can be clamps composed of differing material, for example clamps which are more or less highly radiopaque or else clamps having different magnetic properties especially for differentiation in images taken by magnetic resonance imaging.

Further differentiating features of individual marking devices can also be double-sphere designs.

The material of the caps or sleeves can also be selected in order to achieve certain properties, for example in order to optimize magnetic properties for visibility in magnetic resonance imaging or else to increase X-ray visibility in computed tomography or under C-arms. Suitable materials are, for example, titanium, gold, iron-containing alloys, nitinol, permalloy, mu-metal, neodymium, alnico.

If the two sleeves differ in terms of their shape, in particular length, it is possible to identify better the alignment of the marker in tissue.

Instead of clamps in the narrower sense, which bring about the wire ends being held together by clamping forces, it is also possible to use caps, which are connected to the wire ends by, for example, laser welding or another joining technique Especially caps for holding together the wire ends can be shaped differently and thus bring about individualization.

Suitable materials for the clamps, caps or sleeves are, for example, titanium, gold, iron-containing alloys, nitinol, permalloy, mu-metal, neodymium, alnico, or materials having different magnetic properties, i.e. they can be paramagnetic or diamagnetic and thus be detectable by means of a coil for example.

Furthermore, it is advantageously envisaged that the marking device has no fastening means for the purposes of fixation. This has the advantage that it is possible to dispense with further devices for fixing multiple wires among one another, in particular sleeves or clamps. Additionally or alternatively, the at least one wire can be adhesively bonded, welded or connected in some other suitable way at its contact points. This can be achieved by suitable production methods, in which the at least one wire consisting especially of a superelastic material is brought into a shape required for the support structure. The substantial advantage in the use of superelastic materials such as, for example, nitinol consists in the fact that the region of elastic deformation is substantially larger than in the case of conventional materials.

Furthermore, it is preferably envisaged that the marking device contains hydrogel. To this end, the interior space enclosed by the support structure, even in the preloaded state, can, for example, be filled with a dehydrated hydrogel, which absorbs body fluid or interstitial fluid and swells after deployment of the marking device and expanding of the support structure. A typical swelling factor of such hydrogels, i.e. the volume ratio of dehydrated state to hydrated state, is generally between 1 and 40, but can even assume yet higher values.

This leads to the advantage that the cavity formed by the marking device is uniformly and preferably completely filled with a hydrogel instead of body fluid or interstitial fluid, and thus generates a uniform and reproducible visibility in imaging methods, in particular a dark, hypoechoic appearance in ultrasound methods, which is additionally framed by the bright, hyperechoic image of the wire mesh.

Furthermore, the filling of the cavity with hydrogel prevents the marking device from disadvantageously interacting with adjacent tissue, in particular prevents tissue from entering the marking device. This is particularly advantageous when the marking device resides over a relatively long period within tissue at the tissue site to be marked.

In particular, an interior space filled with hydrogel provides the advantage that the interior space is defined and does not change. In the case of ultrasound-based imaging methods, there is the additional advantage that the combination of a highest possible sound reflection by the support structure and a high sound transmission of the hydrogel leads to a good identifiability of the marking device, since there is highly echogenic tissue in which the hydrogel can be easily seen and precisely not highly echogenic tissue in which the echogenic support structure of the marker is advantageous. Simply the combination of high sound reflection of the support structure and low sound reflection of the interior space generates a contrast, which can be easily identified.

In the case of X-radiation-based imaging methods such as, for example, mammography, a high absorption of X-radiation by the support structure especially in combination with a low absorption of X-radiation by the hydrogel in the interior space enclosed by the support structure leads to a good identifiability in the X-ray image. In the context of a further preferred development, it is envisaged that the marking device in the expanded state has a hollow, ellipsoid shape, where the diameter of the marking device, viewed in the radial direction of a cannula implanting the marking device, in the expanded state is larger than the length of the marking device. This leads to the advantage that the installation force of the support structure during independent transition of the marking device from the compressed state into the expanded state is greater especially in the initial state of the transition. Through the selection of a suitable ratio of ellipsoid diameter to ellipsoid length, it is therefore possible to appropriately determine for a certain tissue a marking device which, after expansion in said tissue and reaching an equilibrium between the expansion force of the support structure and tissue force acting against the expansion of the support structure, assumes an approximately spherical shape. In this way, it is possible, similar to the selection of the wire diameter, to match the expansion force of the support structure of the marking device to various hard or soft tissues in order to achieve a desired marking device shape in the expanded state.

In addition, it is advantageously envisaged that the marking device further contains marking features, for example sleeves of differing shape and/or length, as a supplement to or in addition to the support structure, especially metallic or other radiopaque shaped parts within the support structure. This achieves, inter alia, the advantage that multiple different marking devices implanted in particular at the same time in a patient can be unambiguously, or at least more easily, distinguished in imaging methods. Said shaped parts can, for example, be rods or spheres which are situated within the support structure or fastened to the support structure and which can further have different dimensions for the purposes of better differentiation. Said shaped parts can, for example, be formed from metal.

Preferably, the support structure, for example the wires and/or sleeves thereof, is roughened or texturized, for example by sandblasting, in order to thus increase ultrasound visibility. Alternatively or additionally, the roughing can be performed by means of engraving, in particular laser engraving. In general, a structured surface of a support structure, in particular of the wires and/or sleeves thereof, result in an increased ultrasound visibility. For instance, engraved sleeves can easily increase ultrasound visibility.

The invention is additionally directed to an implantation system comprising a marking device and an implantation device.

The implantation device is designed for the implantation of the marking device according to the invention and comprises a cannula for this purpose. Via the implantation device, the marking device can therefore be advantageously positioned at the tissue site to be marked, especially by using imaging methods, by puncturing the layers of skin and the underlying tissue. Advantageously, it is envisaged that the outer diameter of the cannula of the implantation device is less than 3 mm, preferably between 1.6 mm and 1.2 mm. This leads to the advantage that the implantation of the marking device can be done percutaneously especially because of the low cannula diameter. In particular, a small outer diameter of the cannula allows an implantation of the marking device without being dependent on a stab incision of the skin at the insertion point of the cannula or on an anaesthetization of the tissue concerned.

By means of the complete system, it is possible to operate the marking device together with a suitable and dimensions-matching implantation device. In particular, the implantation system can, as a complete system in the shipped state comprising both marking device and implantation device, contain the marking device already in a compressed state within the cannula, meaning that the method step of compressing the marking device and of preloading the implantation device is omitted for the user and that use is thus further simplified.

Embodiments of the invention will now be described below with reference to the drawing. Said drawing is not necessarily intended to depict the embodiments true to scale; on the contrary, the drawing is, where useful for the purposes of illustration, implemented in schematized and/or slightly distorted form. With respect to additions to the teachings immediately identifiable from the drawing, reference is made to the relevant prior art. In this connection, it should be borne in mind that diverse modifications and changes concerning the form and the detail of an embodiment can be made without deviating from the general concept of the invention. The features of the invention that are disclosed in the description, in the drawing and in the claims can, both individually and in any desired combination, be essential to the development of the invention. Moreover, the scope of the invention covers all combinations of at least two of the features disclosed in the description, the drawing and/or the claims. The general concept of the invention is not restricted to the exact form or the detail of the preferred embodiments shown and described below or restricted to subject matter which would be limited compared to the subject matter claimed in the claims. In the case of specified ranges of dimensions, it is intended that values lying within the stated limits also be disclosed as limit values and be usable and claimable as desired. For the sake of simplicity, the same reference signs are used below for identical or similar parts or for parts of identical or similar function.

BRIEF DESCRIPTION OF THE DRAWINGS

Further advantages, features and details of the invention are revealed by the following description of the preferred embodiments and with reference to the drawing, showing in:

FIG. 2A-B a second variant of a marking device according to the invention in a side view and a front view, FIG. 3A-C an implantation system consisting of implantation device and marking device in total view and detailed view, FIG. 4A-C an implantation system in three implantation situations following one another in a temporal sequence, FIG. 5 a third variant of a marking device according to the invention, FIG. 6 a fourth variant of a marking device according to the invention, FIG. 7 a fifth variant of a marking device according to the invention, FIG. 8a-c a sixth variant of the marking device according to the invention, in which the support structure is formed from a slit tube, in the relaxed state and expanded state, and FIG. 9 the sixth variant of the marking device according to the invention in the laterally compressed state.

DETAILED DESCRIPTION

Figure 1:
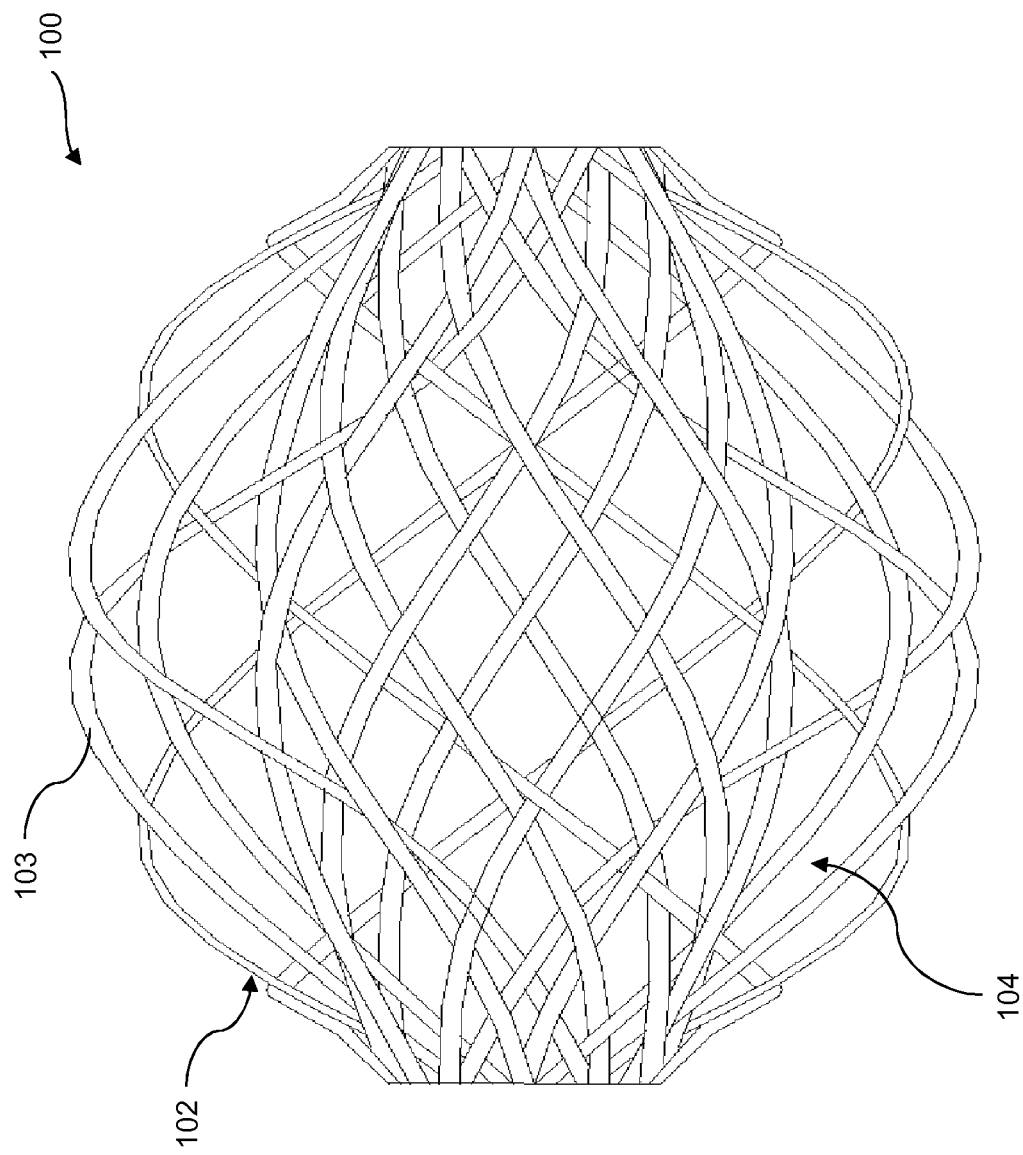
FIG. 1 a first variant of a marking device according to the invention.

FIG. 1 shows a first variant of a marking device 100 according to the invention. The depicted marking device 100 is in the expanded state. It has a support structure 102 which has, in the expanded state, a hollow, approximately spherical shape. The result of this is that the marking device in the expanded state encompasses an interior space 104, which can fill with body fluid in particular. In an improved embodiment, the cavity can be filled with an initially dehydrated hydrogel, which swells through water uptake and uniformly fills out the cavity.

The support structure 102 is formed from at least one wire 103. Said wire can be woven, braided, wound or knitted, or be formed by another appropriate production method to form a support structure 102.

For example, the support structure 102 can be formed by the laying, for example winding, of at least one wire 103, consisting of shape-memory alloy for example, around a shape-forming auxiliary body, the memorization of this shape, for example by means of an appropriate temperature treatment, and the subsequent removal of the auxiliary body. In this case, the at least one wire 103 can be laid such that the result is, for example, a cruciform or honeycombed structure in which wire sections cross repeatedly for example. Alternatively, the at least one wire can be laid in an unstructured manner, for example in the manner of a ball of thread, around the shape-forming auxiliary body.

Alternatively or additionally, the contact points of the at least one wire 103 can be welded among one another for the purposes of fixation or connected to one another via an appropriate alternative method.

The support structure 102 encompasses an interior space 104, which can be empty or filled with, for example, hydrogel, polymer foam or suture material, i.e. preferably with a material having a high transparency for ultrasound.

FIG. 2A shows one variant of a marking device 100' according to the invention. In said marking device, the support structure 102' is formed from a multiplicity of wires 103', which are held together at their longitudinal ends by, in each case, a clamp 105' in a clamping zone 106'. The clamp 105' has a length LK, which can, for example, assume a value between 0.5 mm and 3 mm, preferably between 0.5 mm and 1.0 mm. The greater the length LK, the more stable in general the fixation of the wires, though at the same time the proportion of the volume not contributing to the visibility of the characteristic shape of the marking device also increases. Therefore, a decrease in market acceptance of the marking device has to be assumed with an increase in length LK.

In the exemplary embodiment in FIG. 2, the clamp 105' is designed as a sleeve. Alternatively, the clamp can also have other shapes, for example be designed as a cap. The clamps can thus differ from one another in terms of shape and length for example. This makes it possible to use marking devices having different clamps, meaning that individual marking devices can also be individually identified after implantation.

Preferably the clamp, in particular if the clamp is a sleeve, is textured, e.g. engraved, for instance laser engraved, in order to increase ultrasound visibilty.

Further differentiating features of individual marking devices can be clamps composed of differing material, for example clamps which are more or less highly radiopaque or else clamps having different magnetic properties especially for differentiation in images taken by magnetic resonance imaging.

Accordingly, individual wires 103' of the support structure 102' can also consist of a different material than the other wires in order to individualize marking devices or else in order to produce certain features in various imaging methods.

Instead of clamps in the narrower sense, which bring about the wire ends being held together by clamping forces, it is also possible to use caps, which are connected to the wire ends by, for example, laser welding or another joining technique.

Especially caps for holding together the wire ends can be shaped differently and thus bring about individualization.

Suitable materials for the clamps, caps or sleeves are, for example, titanium, gold, iron-containing alloys, nitinol, permalloy, mu-metal, neodymium, alnico, or materials having different magnetic properties, i.e. they can be paramagnetic or diamagnetic and thus be detectable by means of a coil for example.

Furthermore, the marking device 100 has a length LM, which specifies the spread of the total marking device in the axial direction. In this development, said length is formed from the length of the support structure 102, and the lengths LK of the two clamps 105. If the support structure of the marking device is fixed by, for example, welding of the at least one wire instead of with clamps, the length LM changes accordingly. The length LM can, for example, assume a value between 3 mm and 9.5 mm, preferably between 3 mm and 6 mm.

The marking device 100 has a diameter DM, which is formed by the radial expansion of the support structure 102 in the expanded state. Said expanded state of the marking device 100 is achieved by its support structure 102 consisting of at least one wire 103 spreading, after deployment from the cannula 242 of the implantation device 200, against a tissue pressure prevailing at the tissue site to be marked, and thus passing from the laterally compressed state into the expanded state.

This independent expansion is achieved by the support structure 102 being formed from a material having a high elasticity, more particularly superelastic behaviour. More particularly, said behaviour can be achieved by the use of a superelastic material, for example nitinol.

In the compressed state of the support structure 102, the diameter DM of the marking device 100 assumes a low value, more particularly a value less than or equal to the inner diameter DKI of the cannula 242 of the implantation device 200.

FIG. 2B depicts the marking device 100 in a front view. In said view, it is possible to see the front view of one of the two clamps 105, in which the wires 103 of the support structure 102 have been fixed together. In this development, the support structure consists of 24 individual wires, which have been fixed in parallel alignment in a clamping zone 106 and the end faces of which can be seen in said front view.

The clamp 105 has a diameter DK, which can, for example, assume a value between 0.6 mm and 2.1 mm, preferably between 0.6 mm and 1.2 mm. The diameter DK influences the smallest possible cannula diameter of the implantation device 200, by means of which the marking device 100 is implanted in tissue. The larger the diameter DK, the larger the diameter of the cannula 242 also needs to be in order to ensure pass-through ability when preloading and deploying the marking device 100.

FIG. 3A depicts an implantation system 300 comprising a marking device 100 and an implantation device 200. Here, the marking device 100 is in the preloaded state, i.e. with compressed support structure 102, within the cannula 242 of the implantation device 200. This state of the implantation system 300 represents a typical shipped state, providing the implantation system ready for use by the user, for example a surgeon.

The implantation part 240 of the implantation device 200 essentially consists of a cannula 242, having at the front end, on the side facing away from the handle 210, a cannula tip 244. In this region within the cannula 242, just before the outlet at the cannula tip 244, the marking device 100 is generally in the preloaded state. The cannula 242 can be formed particularly from a suitable metal.

The cannula 242 has a length LKA, which can, for example, assume a value between 25 mm and 200 mm, preferably between 50 mm and 150 mm. The length LKA of the cannula 242 influences the reach of the implantation device 200 with respect to the accessibility of tissue sites in the body of a patient that are to be marked. When using adjusting aids, for example in stereotaxy, longer cannulas are used.

Furthermore, the implantation device 200 comprises a handle 210 and an implantation part 240. The handle 210 in turn comprises a handle housing 212 and a sliding element 214, which can, for example, be produced from a suitable plastic.

The sliding element 214 is connected to the handle housing 212, but is movable relative to the handle housing 212 in the axial direction of the cannula 242. Therefore, the sliding element 214 can be moved on a straight, guided sliding path between a preload position 218 and a deployment position 220.

This movement is transferred from the sliding element 214, via a deployment element 216 which is connected to the sliding element 214 and which can, for example, be formed via a wire or a sufficiently stable plastics fibre, into the front region facing away from the handle 210. Therefore, upon movement of the sliding element 214 into the deployment position 220, the preloaded marking device 100 can be deployed, by means of a sliding movement of the deployment element 216, from the cannula 242 to the tissue site to be marked at the distal end of the cannula 242.

This is achieved by the deployment element 216 aligned coaxially in relation to the cannula 242 moving in the direction of the cannula tip 244 and hence sliding the preloaded marking device 100 past the cannula tip 244 out of the cannula 242.

FIG. 3B depicts detail B from FIG. 3A, specifically a detailed view of the implantation system 300 in the preloaded state, in the region of the cannula tip 244. In said view, it is possible to see in particular the marking device 100 in the laterally compressed state, which marking device 100 is situated, from the perspective of the handle 210, behind the deployment element 216 and in front of the cannula tip 244 within the cannula 242. Owing to its pretension, the marking device 100 retains its position in the cannula 242 and cannot fall out independently. This property means that it is possible to dispense with additional features or devices for the fixation of the marking device 100 within the cannula 242.

FIG. 3C shows in turn, as detail C from FIG. 3B, a more detailed, schematic view of the cannula 242. In said view, it is possible to see the distal end of the deployment element 216 within the cannula 242. Furthermore, the outer diameter DKA and the inner diameter DKI of the cannula 242 are labelled.

The inner diameter DKI of the cannula 242 describes, together with the cannula length LKA, the size of the inner cavity formed by the cannula 242 and limits at the same time the maximum possible diameter DM of the marking device 100 in the laterally compressed state or possibly the maximum possible diameter DK of the at least one clamp 105 in order to ensure a pass-through ability or mobility of the marking device 100 within the cannula 242 during preloading and deployment. An inner diameter DKI of less than 1.1 mm, particularly preferably of 1.0 mm, has been found to be preferable.

The outer diameter DKA of the cannula 242 describes the diameter of the outer cannula wall. With an increasing outer diameter DKA, the inner diameter DKI of the cannula 242 simultaneously increases, assuming a constant, smallest possible cannula wall thickness, and so does the maximum possible outer diameter of a marking device 100 to be implanted. However, at the same time, an increasing outer diameter DKA leads to a higher degree of invasiveness or injury of skin and tissue when carrying out the implantation.

A sufficiently small outer diameter DKA ensures the possibility of a percutaneous implantation of the marking device 100 without being dependent on a stab incision of the skin at the insertion point of the cannula 242 or on an anaesthetization of the tissue concerned. An outer diameter DKA between 1 mm and 1.5 mm, particularly preferably of 1.2 mm, has been found to be preferable.

Figure 4A:
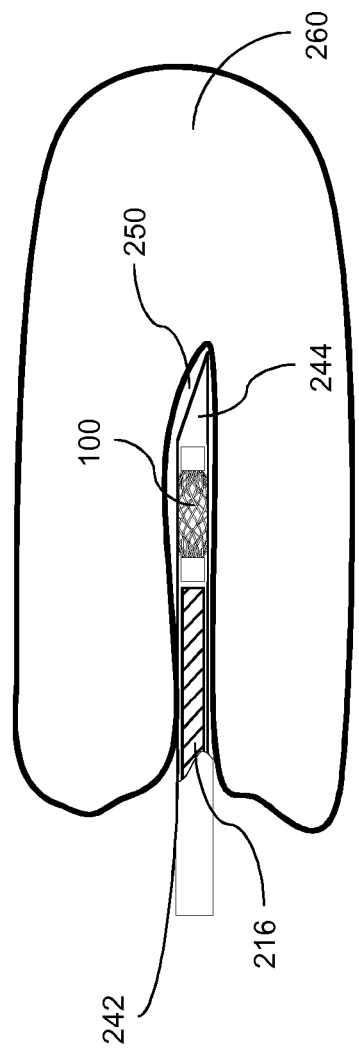
Figure 4B:
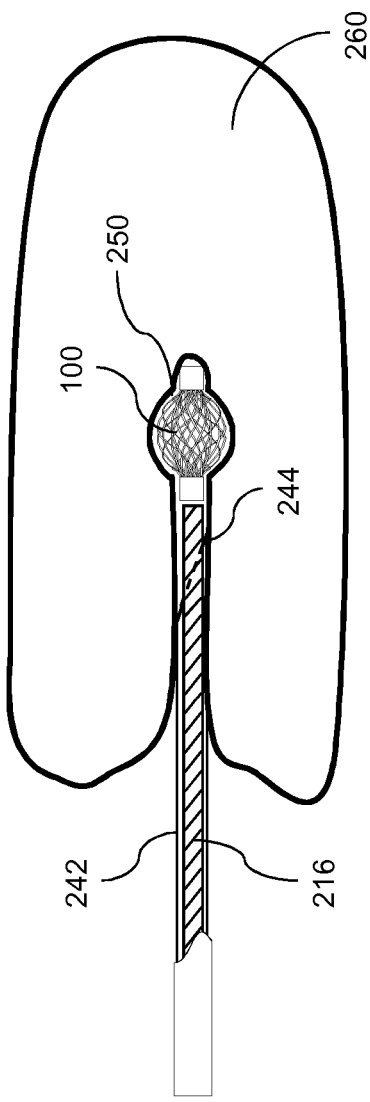
Figure 4C:
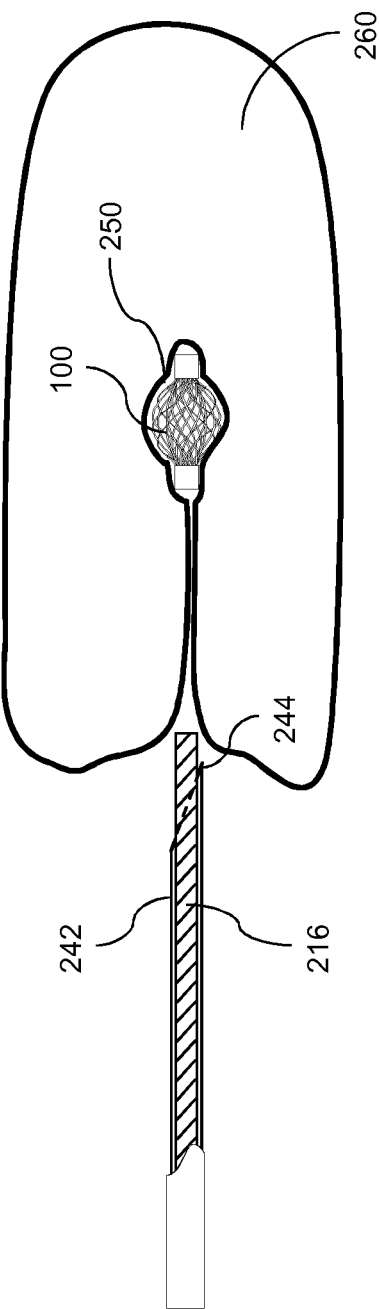

FIGS. 4A-C depict schematically an implantation system 300 in three implantation situations following one after another in time, with each situation showing part of the implantation system: in each situation, the distal end of an implantation device 200 in a tissue 260 is depicted.

In FIG. 4A, the implantation system 300 is in the pre-loaded state, specifically with a cannula 242 containing a compressed marking device 100, said cannula 242 being positioned such that the cannula tip 244 is situated at the site 250 of the tissue 260 that is to be marked. This positioning of the cannula tip 244 is generally effected by the user, for example a surgeon, with the aid of imaging methods, for example ultrasound.

FIG. 4B depicts a subsequent step, in which the marking device 100 is, by forward sliding of the deployment element 216 and withdrawal of the cannula 242, slid past the cannula tip 244 out of the cannula 242 and is thus deployed at the tissue site 250 to be marked. In the course of this, the marking device 100 expands itself so as to pass from a laterally compressed state into an expanded state, through expanding of the support structure 102 even against a tissue pressure acting on the marking device 100 at the site 250 to be marked.

FIG. 4C lastly depicts how the implantation device 200 is, after deployment of the marking device 100, removed from the site 250 in the tissue 260 that is to be marked and finally from the body of the patient by withdrawal of the cannula 242 and of the deployment element 216. In the course of this, the marking device 100 remains in the expanded state at the tissue site 250 to be marked. The channel formed by the cannula 242 from the insertion point at the skin to the tissue site 250 to be marked normally closes again after removal of the implantation device 200 from the body of the patient.

In a further embodiment of the implantation system, the cannula 242 is connected to the sliding element 214 and the deployment element 216 is connected to the handle housing 212. Thus, the relative movement required in order to deploy the marking device 100 is generated by a withdrawal of the sliding element 214. In the course of this, the deployment element 216 remains at its position and likewise holds the marking device 100 at its position during the backward movement of the cannula 242. This has the advantage that the marking device 100, after positioning by means of the implantation device 100, no longer alters its position. The risk of an unfavourable positioning at a position deviating from the tissue site 250 to be marked can thus be reduced. Furthermore, the marking device 100 remains at the end of the pierce channel in this case and is, upon deployment, not pressed against uninjured tissue and/or deformed.

Figure 5:
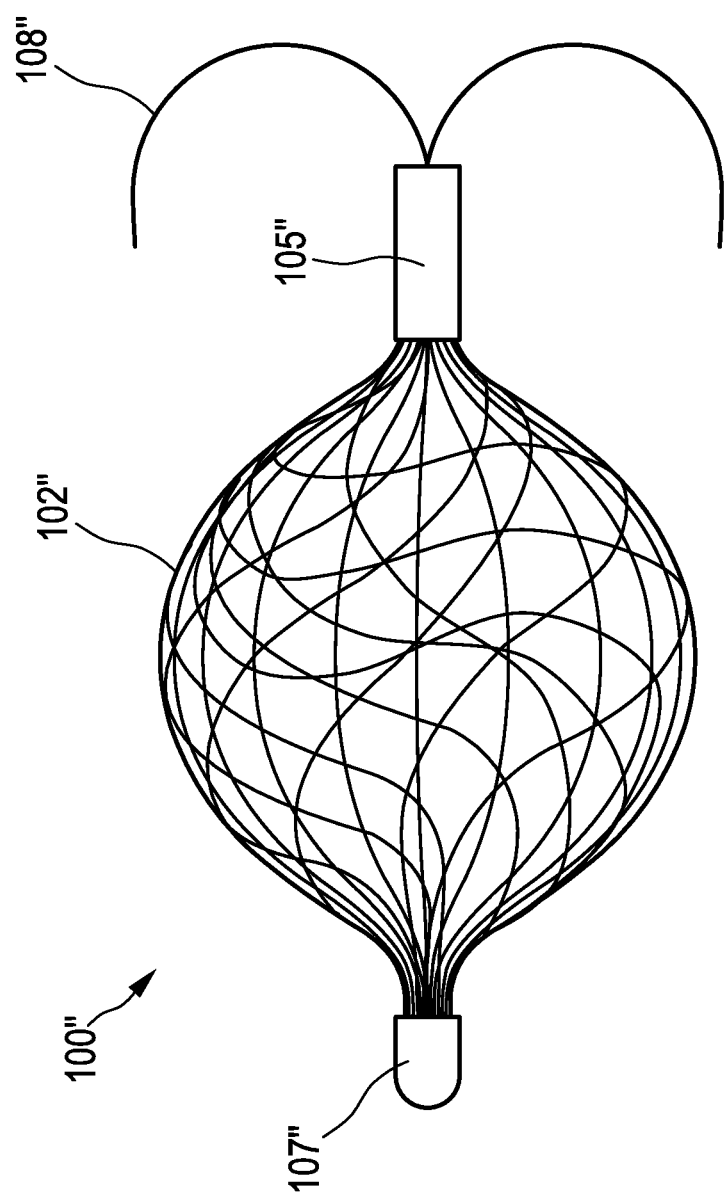

FIG. 5 shows a third variant of an inventive marking device 102', the support structure 102" of which is formed by a multiplicity of wires 103'", which are connected to another at one longitudinal end of the mark using a cap 107" acting as a clamp. At the other end of the marking device 100" on the right of the figure, the wires 103" are connected to one another using a clamp 105" at a slight distance from their particular longitudinal end, such that longitudinal ends 108" project beyond the clamp 105" as free longitudinal ends. Said free longitudinal ends 108" are bent in a hook-shaped manner and thus support a secure anchoring of the marking device 100" in tissue. Furthermore, the marking device 100" displayed in FIG. 5 can easily be palpated in the tissue by a physician after implantation.

Figure 6:
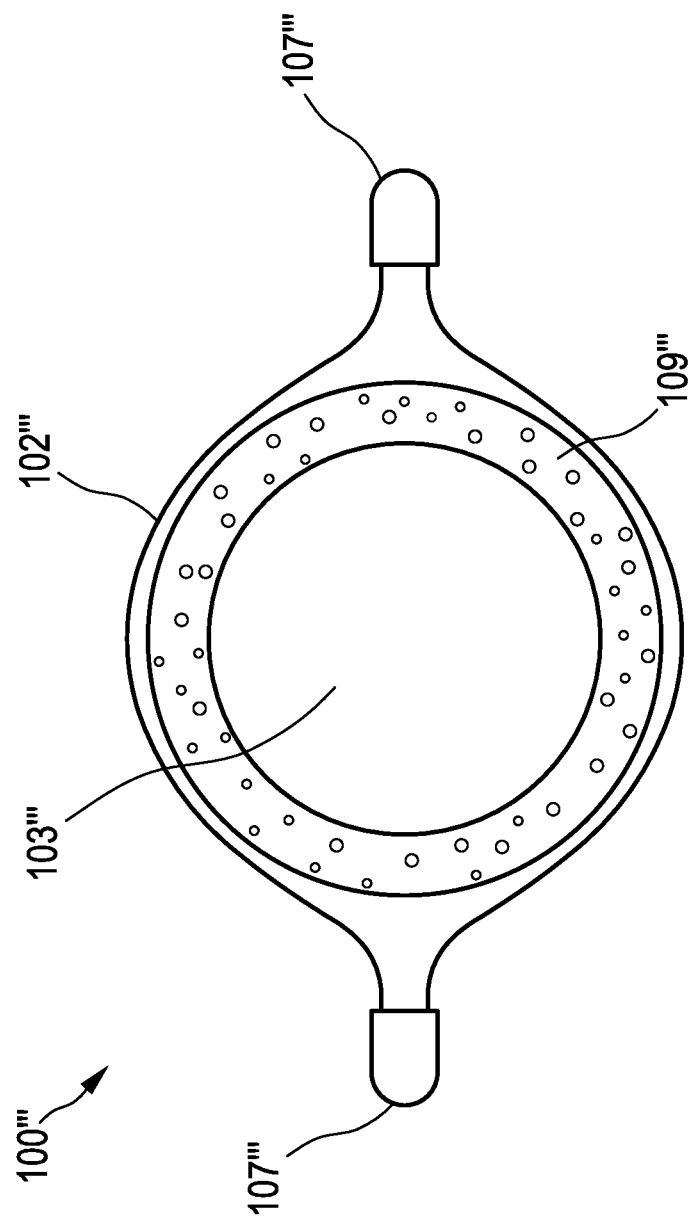

FIG. 6 shows a fourth variant of an inventive marking device 100'", whose interior space 104'" encompassed by the support structure 102'" is surrounded by a material layer 109'" which is in contact with the support structure 102'" and encompasses a hollow interior space 104'". The material layer 109'" can, for example, contain air bubbles, particles of hydrogel or a combination of these constituents in order to thus influence the visibility of the marking device 100'" under ultrasound or in X-ray. To influence the visibility of the marking device 100'" in magnetic resonance imaging, the layer can consist of a metamaterial which eliminates or modifies susceptibility artefact in magnetic resonance imaging.

Figure 7:
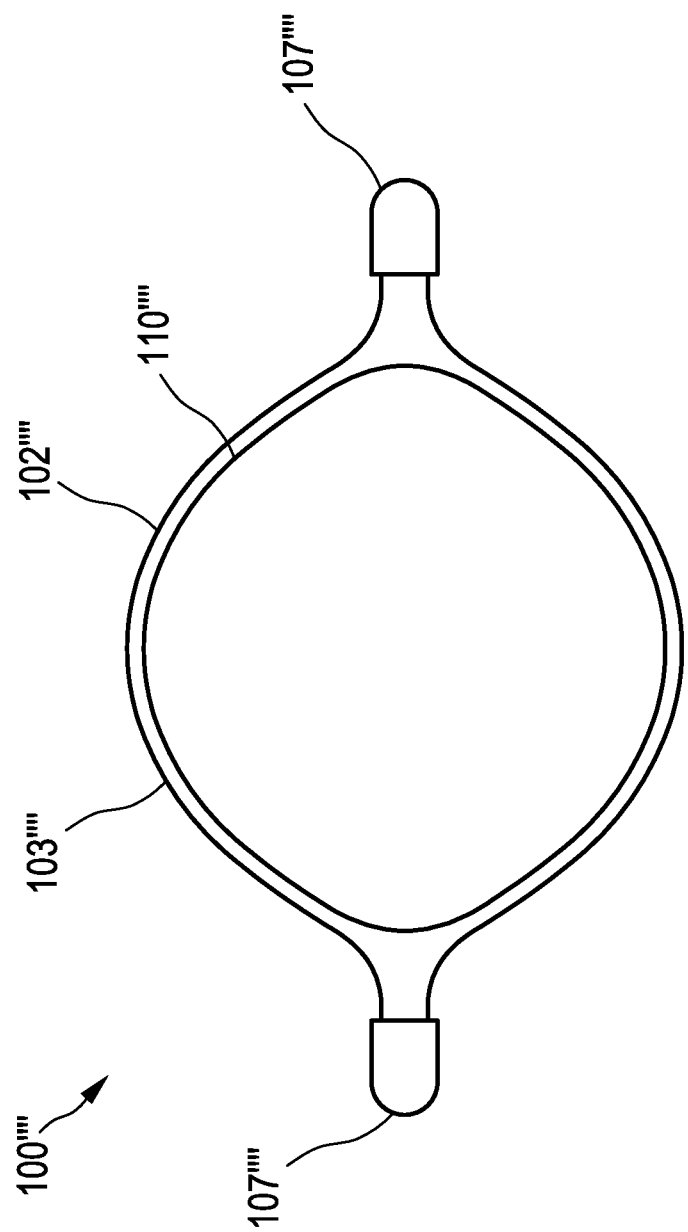

FIG. 7 shows a fifth variant of an inventive marking device 100"", whose interior space 104"" is enclosed by a membrane 110"" which is held in position against the inside of the support structure 102"". Suitable materials for such a membrane 110"" are, for example, silicone or polyurethane. The membrane 110"" can be filled with hydrogel or ICG (indocyanine green), magnetic nanoparticles, a fluorescent medium, medicaments, cells or radioisotopes or a combination of these ingredients. Instead of fitting it on the inside of the support structure 102"", the membrane can surround the support structure on the outside. Such a membrane entails the advantage that the interior space encompassed thereby alters as little as possible over the course of time.

Figure 8:
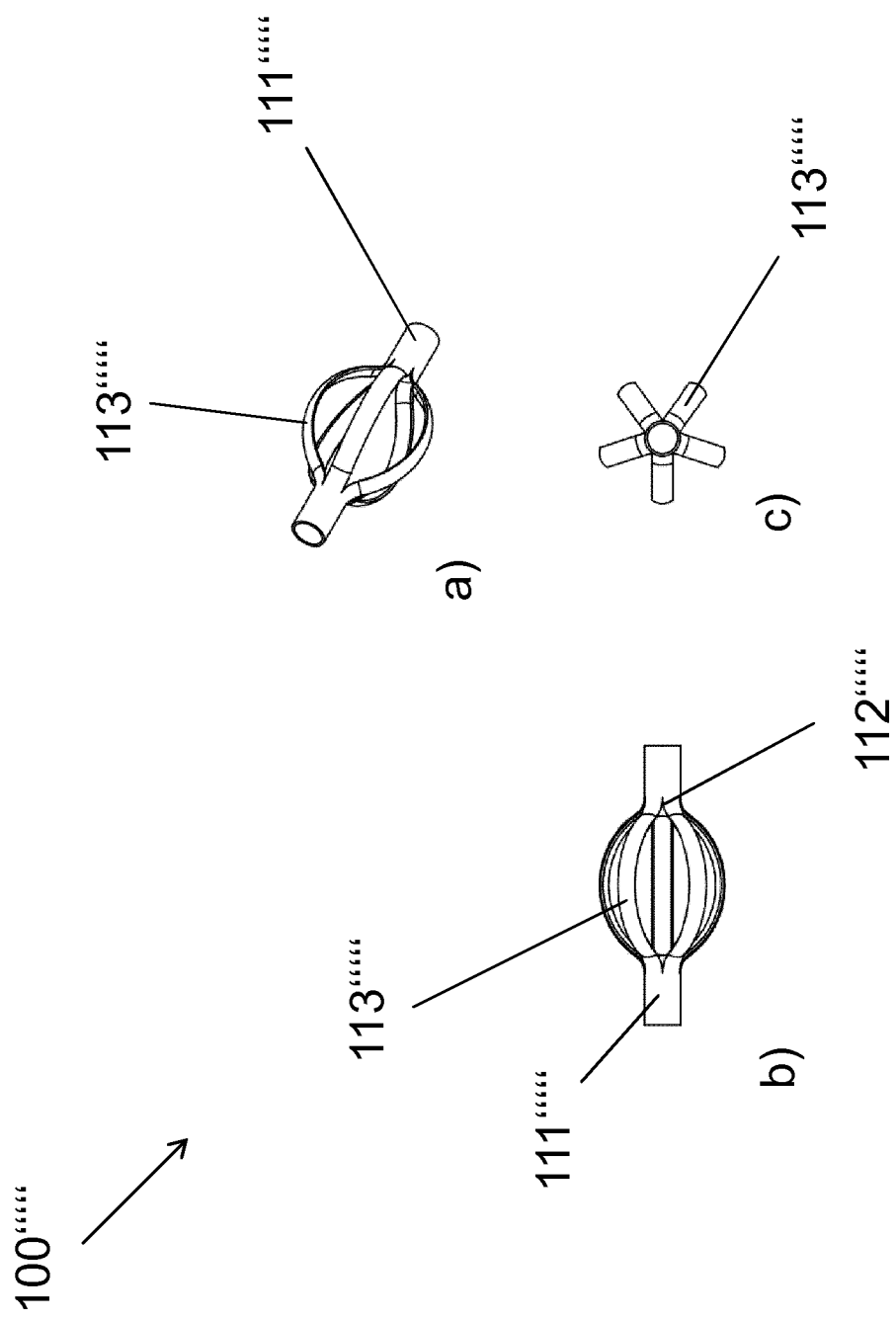

FIGS. 8a to 8c show various views of a sixth variant of a marking device 100""', the support structure 102""' of which is formed by a slit tube 111""'. Since the longitudinal ends 112""' of the tube 111""' are not slit, the support structure does not require any end-caps or clamps. However, they can nevertheless be provided, for example for marking purposes. Segments 113""' separated from one another by slits 112""' arch outward in the relaxed, expanded state of the marking device 100""' and thus encompass an interior space 103""' which is, for example, approximately spherical. As in the other exemplary embodiments, said interior space can be empty or filled with, for example, hydrogel, polymer foam or suture material or enclosed by a membrane or a material layer.

FIG. 8a is a perspective view of the sixth variant of the marking device 100""', FIG. 8b is the side view thereof and FIG. 8c is the end-face view thereof.

Figure 9:
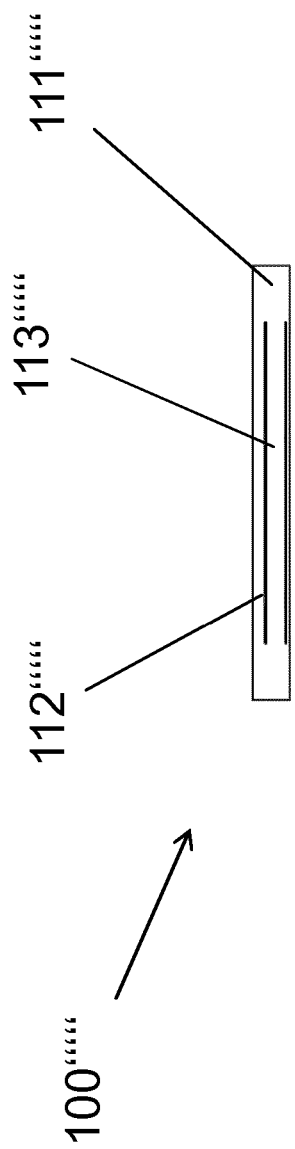

FIG. 9 shows the sixth variant of the marking device 100""' in the compressed state, in which it is easy to identify that the marking device 100""' is made from a slit tube. The marking device 100""' can be produced such that the tube 111""' is first provided with slits 112""' and then axially compressed in the longitudinal direction such that the segments 113""' bend outward and, in doing so, deform in a plastic manner, meaning that the relaxed state of the marking device 100""' is that having outwardly arched segments 113""', as displayed in FIGS. 8a to 8c. In its relaxed state, marking device 100""' is thus axially compressed and laterally expanded. Preferably, tube 111""' is textured so as to increase ultrasound visibility. In particular, the tube can be engraved, for instance laser engraved.

In an unshown modification of the exemplary embodiment displayed in FIGS. 8a to 8c, only one longitudinal end of the tube is unslit, meaning that the segments separated from one another by the slits each have a free longitudinal end. Said free longitudinal ends of the segments can then in turn by held together by a sleeve or a cap. In this way, it is also possible to generate a marking device similar to the one from FIG. 5.

LIST OF REFERENCE SIGNS

100 Marking device
102 Support structure

103 Wire
104 Interior space
105 Clamp
106 Clamping zone
107 Cap
108 Free longitudinal end
109 Material layer
110 Membrane
111 Tube
112 Slit
113 Segment
DK Diameter of clamp
LK Length of clamp
LM Length of marking device
DM Diameter of marking device
DKI Inner diameter of cannula
DKA Outer diameter of cannula
LKA Length of cannula
200 Implantation device
210 Handle
212 Handle housing
214 Sliding element
216 Deployment element
218 Preload position
220 Deployment position
240 Implantation part
242 Cannula
244 Cannula tip
250 Tissue site to be marked
260 Tissue
300 Implantation system

What is claimed is:

1. A marking device for implantation into a tissue, comprising:
 a support structure configured to transition between a compressed state and an expanded state, the support structure being formed from at least one elastic metal wire, the at least one elastic metal wire comprising a plurality of overlapping wire sections,
 wherein in the expanded state, the support structure has a rounded shape encompassing an interior space.

2. The marking device according to claim 1, wherein the support structure is woven, braided, wound or knitted.

3. The marking device according to claim 1, wherein all wire ends of the support structure are located within the interior space of the support structure.

4. The marking device according to claim 1, wherein a diameter of the at least one elastic metal wire is less than about 0.5 mm.

5. The marking device according to claim 1, wherein a diameter of the support structure in the expanded state is less than about 8 mm.

6. The marking device according to claim 1, wherein a diameter of the support structure in the compressed state is less than about 3 mm.

7. The marking device according to claim 1, wherein the at least one elastic metal wire comprises nitinol.

8. The marking device according to claim 1, further comprising, at least one a fastener for fixing the support structure in the tissue.

9. The marking device according to claim 8, wherein the at least one elastic metal wire includes a free end configured to anchor the marking device in the tissue.

10. The marking device according to claim 1, wherein the interior space contains hydrogel, polymer foam or surgical suture material.

11. The marking device according to claim 1, wherein the marking device has a membrane which is in contact with the support structure.

12. The marking device according to claim 1, wherein the interior space is surrounded by a material layer.

13. The marking device according to claim 1, wherein, in the expanded state, the support structure has a hollow, ellipsoid shape, and wherein a diameter of the marking device in the expanded state, viewed in a radial direction of a cannula implanting the marking device, is larger than a length of the marking device.

14. The marking device according to claim 1, wherein the marking device further contains marking features as a supplement to or in addition to the support structure, the marking features comprising metallic and/or other radiopaque shaped parts within the support structure.

15. The marking device according to claim 1, wherein the wire sections cross repeatedly to form a pattern.

16. The marking device according to claim 1, wherein the at least one elastic metal wire comprises a plurality of wires, each of the plurality of wires having first and second ends, wherein the plurality of wires are secured to one another by a clamp or cap at the first and/or second ends.

17. The marking device according to claim 1, wherein the at least one elastic metal wire comprises a plurality of wires, the plurality of wires comprising a first wire made from a first material and a second wire made from a second material, different from the first material.

18. The marking device according to claim 1, wherein, in the expanded state, the support structure has a hollow, spherical shape.

19. The marking device according to claim 1, wherein, during implantation into the tissue, in the expanded state, the support structure fills a surgical cavity.

20. An implantation system comprising:
 a marking device according to claim 1; and
 an implantation device comprising a cannula, the marking device being located within the cannula and configured to move out of the cannula by actuation of the implantation device.

21. The implantation system according to claim 20, wherein the implantation system is configured for use within a vacuum biopsy unit.

* * * * *